US00PP22647P2

(12) United States Plant Patent
Jones

(10) Patent No.: US PP22,647 P2
(45) Date of Patent: Apr. 10, 2012

(54) ***SALVIA* PLANT NAMED 'CATHEDRAL SKY LAVENDER'**

(50) Latin Name: *Salvia farinacea*
Varietal Denomination: CATHEDRAL SKY LAVENDER

(76) Inventor: Steve Jones, Santa Monica, CA (US)

( * ) Notice: Subject to any disclaimer, the term of this patent is extended or adjusted under 35 U.S.C. 154(b) by 0 days.

(21) Appl. No.: 12/799,988

(22) Filed: May 5, 2010

(51) Int. Cl.
*A01H 5/00* (2006.01)

(52) U.S. Cl. ..... Plt./475

(58) Field of Classification Search ..... Plt./475
See application file for complete search history.

*Primary Examiner* — June Hwu
(74) *Attorney, Agent, or Firm* — Cassandra Bright

(57) ABSTRACT

A new and distinct *Salvia* cultivar named 'CATHEDRAL SKY LAVENDER' is disclosed, characterized by having distinctive lavender flowers, a compact, very well-branched plant habit, and early, flowering. The new variety is a *Salvia*, normally produced as an outdoor garden or container plant.

1 Drawing Sheet

Figure 1:
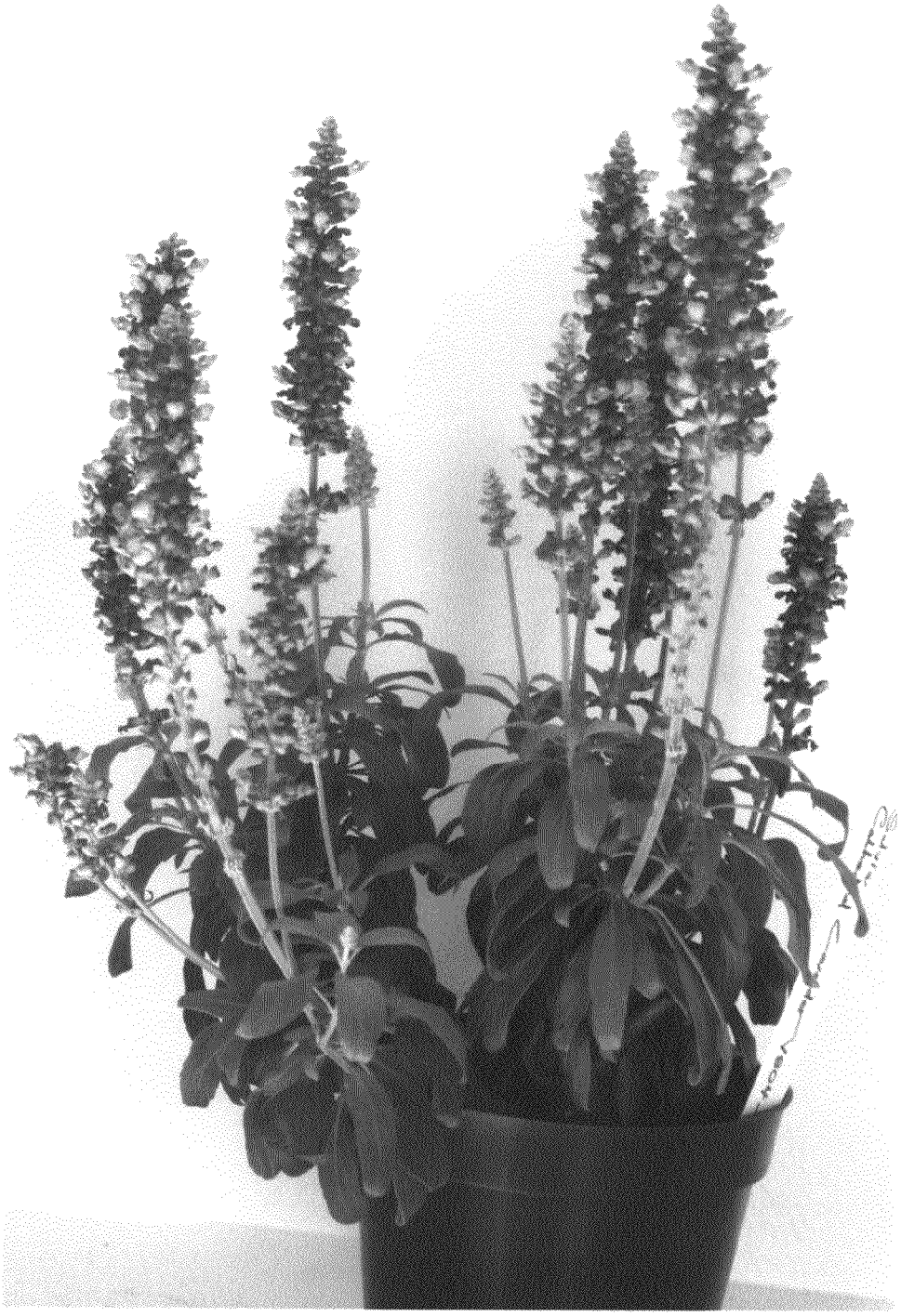

Latin name of the genus and species: *Salvia farinacea.*

Variety denomination: 'CATHEDRAL SKY LAVENDER'.

BACKGROUND OF THE INVENTION

The new cultivar was discovered as a spontaneous whole plant mutation by the inventor, Steve Jones. The parent variety is the unpatented, variety *Salvia farinacea* 'Signum.' The new variety was discovered January 2000, by the inventor in a commercial planting of approximately 100,000 plants of *Salvia farinacea* 'Signum' in Quillota, Chile.

Asexual reproduction of the new cultivar 'CATHEDRAL SKY LAVENDER' by vegetative cuttings was first performed January 2000, at a commercial greenhouse in Quillota, Chile and has shown that the unique features of this cultivar are stable and reproduced true to type on successive generations.

SUMMARY OF THE INVENTION

The cultivar 'CATHEDRAL SKY LAVENDER' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'CATHEDRAL SKY LAVENDER'. These characteristics in combination distinguish 'CATHEDRAL SKY LAVENDER' as a new and distinct *Salvia* cultivar:

1. Compact plant habit.
2. Lavender flowers.
4. Early flowering.

PARENT COMPARISON

Plants of the new cultivar 'CATHEDRAL SKY LAVENDER' are similar to plants of the parent, *Salvia farinacea* 'Signum' in most horticultural characteristics, however, plants of the new cultivar 'CATHEDRAL SKY LAVENDER' are shorter. Additionally, flowers of the parent variety are dark Lavender, to purple whereas, the new variety produces distinct, light lavender flowers, and have a longer panicle.

COMMERCIAL COMPARISON

Plant of the new cultivar are best compared to the commercial variety *Salvia farinacea* 'CATHEDRAL SKY BLUE,' U.S. Plant Pat. No. 20,929. Plants of the new variety are slightly taller and more spreading. 'CATHEDRAL SKY LAVENDER' also produces blooms colored more lavender than blue-lavender.

BRIEF DESCRIPTION OF THE PHOTOGRAPH

The accompanying photograph in FIG. 1 illustrates in full color a typical plant of 'CATHEDRAL SKY LAVENDER' grown in a greenhouse, in Lompoc, Calif., in a commercial 6 inch container. Age of the plant photographed is approximately 20 weeks from an unrooted cutting. The photograph was taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart, 2001 except where general terms of ordinary dictionary significance are used. The following observations and measurements describe 'CATHEDRAL SKY LAVENDER' plants grown in a greenhouse in Lompoc, Calif. The growing temperature ranged from 20° C. to 28° C. The greenhouse is un-shaded, giving bright, normal sunlight conditions. Measurements and numerical values represent averages of typical plant types.

Botanical classification: *Salvia farinacea* cultivar 'CATHEDRAL SKY LAVENDER.'

PROPAGATION

Time to initiate roots: About 5-8 days at approximately 25° C.
Root description: Fine, densely fibrous.
Time to produce a rooted cutting: About 21 days at 25° C.

PLANT

Growth habit: Upright annual.
Pot size of plant described: 6 inch pot
Height: Approximately 17 cm to top of foliage. Approximately 40 cm to top of flowering plane. Measured from soil level of pot.
Plant spread: Approximately 33 cm.
Growth rate: Rapid.
Branching characteristics: Free-branching, Approximately 4 primary branches.
Length of primary lateral branches: Approximately 8 cm.
Diameter of lateral branches: Approximately 0.5 cm
Quantity of lateral branches: About 16.
Stem:
*Color.*—Near RHS Green 138 B.
*Pubescence.*—Very slight pubescence.
Internode length: Approximately 2.5 cm.
Age of plant described: Approximately 20 weeks from an unrooted cutting.

FOLIAGE

Leaf:
*Arrangement.*—Opposite, mainly. Many upper nodes have multiple, single leaves emerging from same node, in an opposite pattern.
*Quantity.*—Approximately 14 per main branch.
*Average length.*—Approximately 5.0 cm.
*Average width.*—Approximately 1.9 cm.
*Shape of blade.*—Lanceolate.
*Apex.*—Acute.
*Base.*—Attenuate.
*Attachment.*—Stalked.
*Margin.*—Nearly entire, with infrequent dentations.
*Texture of top surface.*—Matte.
*Texture of bottom surface.*—Slightly pubescent.
*Color.*—Young foliage upper side: Near RHS Green 137B. Young foliage under side: Near RHS Green 138A. Mature foliage upper side: Near RHS Green 137A. Mature foliage under side: Near RHS Green 138A.
*Venation.*—Type: Pinnate. Venation color upper side: Near RHS Green 143C. Venation color under side: Near RHS Yellow-Green 144D.
*Petiole.*—Average Length: Approximately 0.7 cm. Diameter: Approximately 0.1 cm. Color: Near Yellow-Green 144D.

FLOWER

Natural flowering season: Begins flowering between 6 and 7 weeks from planting a rooted cuttings. Flowering continues from early Spring through late Summer.
Inflorescence type and habit: Flowers arranged in verticillasters on spikes.
Flower longevity on plant: Individual flowers last 5 days on the plant. Each spike lasts approximately 6 weeks with flowers.
Quantity of flowers: About 30 buds and 20 fully opened flowers per lateral branch, at one time.
Inflorescence size:
*Diameter.*—Approximately 3.5 cm.
*Height.*—Approximately 16 cm.
Peduncle:
*Length.*—Averages 6-8 cm.
*Diameter.*—0.5 cm.
*Color.*—Near RHS Purple 79D.
*Orientation.*—Upright, straight.
*Strength.*—Strong.
*Texture.*—Pubescent.
Corolla:
*Petal arrangement.*—The corolla is sympetalous and typically bilabiate with 2 small, highly fused lobes forming an upper lip and 3 larger highly fused lobes forming a lower lip.
*Margin.*—Nearly entire, slightly scalloped.
*Tip shape.*—Upper lip tip retuse, lower lip tip rounded with scallops.
*Length.*—Upper lip Approximately 0.6 cm, lower lip Approximately 1.1 cm.
*Width.*—Upper lip Approximately 0.4 cm, lower lip Approximately 1 cm.
*Petal quantity.*—One upper lip and one lower lip with three lobes. Upper lips are entirely fused at base.
*Texture.*—Upper lip has short, feather-like hairs, lower lip is smooth and hairless.
*Aspect.*—75 to 90° stem.
*Petaloids.*—Upper lip has 2 petaloids, lower lip has 4 petaloids.
*Petaloid length.*—Approximately 0.2 cm.
*Petaloid diameter.*—Approximately 0.2 cm.
*Petaloid shape.*—Irregular ovate.
*Petaloid color.*—Near RHS Violet 85B.
Color:
*Petals.*—When opening: Upper surface: Apex Near RHS Violet 86C, base Near RHS Violet 85B. Lower surface: Apex Near RHS Violet 86C, base Near RHS Violet 85D. Fully opened: Upper surface: Near RHS Violet 85C, margins Near RHS Violet 86D. Lower surface: Near RHS Violet 85C, margins Near RHS Violet N88B. Fading: Upper surface: Near RHS Violet 85A, margins Near RHS Violet N88B. Lower surface: Near RHS Violet 85B, margins Near RHS Violet N88B.
Bud:
*Shape.*—Ovoid.
*Length.*—Approximately 0.4 cm.
*Diameter.*—Approximately 0.2 cm.
*Color.*—Near RHS Violet 86B.
Calyx:
*Length.*—Approximately 0.6 cm.
*Diameter.*—Approximately 0.4 cm.
*Shape.*—Tubular.
Sepals:
*Shape.*—Quantity per flower: 2, fused to form a tube.
*Length.*—Approximately 0.6 cm.
*Width.*—Approximately 0.4 cm.
*Margin.*—Entire.
*Texture.*—Pubescent.
*Color.*—Immature: Near RHS Violet 85B. Mature: Near RHS Violet 86B.
*Calyx tube color.*—Immature: Near RHS Violet 85A. Mature: Near RHS Violet 86B.

*Quantity.*—2 at the base of each verticillaster.
*Shape.*—Deltoid.
*Tip.*—Accuminate.
*Texture.*—Lightly pubescent.
*Length.*—Approximately 0.4 cm.
*Width.*—Approximately 0.2 cm.
*Color.*—Upper surface: Near RHS Violet 86B. Lower surface: Near RHS Violet 86D.

Persistence: Non-persistent.

Fragrance: Very faint fragrance, non aromatic *Salvia*

REPRODUCTIVE ORGANS

Stamens:
*Number.*—2.
*Filament length.*—Approximately 0.4 cm.
*Filament color.*—Near RHS N155A.

Anthers:
*Shape.*—Very narrowly elliptic.
*Length.*—Approximately 1 mm.
*Color.*—Near RHS Purple 79A.
*Pollen.*—Pollen production not observed.

Pistil:
*Number.*—1.
*Length.*—Approximately 1.1 cm.
*Style.*—Length: Approximately 0.8 cm. Color: Near RHS N155A.
*Stigma.*—Shape: Linear, curled. Color: Near RHS N155A. Ovary color: Near RHS N155A.

OTHER CHARACTERISTICS

Seeds and fruits: Not observed to date.

Disease/pest resistance: Neither resistance nor susceptibility to pathogens and pests common to *Salvia* have been observed.

Temperature tolerance: The new variety tolerates temperatures between 5 to 35° C.

What is claimed is:

1. A new and distinct cultivar of *Salvia* plant named 'CATHEDRAL SKY LAVENDER' as herein illustrated and described.

* * * * *